(12) United States Patent
Yang et al.

(10) Patent No.: US 12,385,992 B2
(45) Date of Patent: Aug. 12, 2025

(54) MAGNETIC RESONANCE SYSTEM AND MAGNETIC RESONANCE SCANNING CONTROL METHOD

(71) Applicant: GE Precision Healthcare LLC, Waukesha, WI (US)

(72) Inventors: Fan Yang, Beijing (CN); Qingyu Dai, Beijing (CN); Kun Wang, Beijing (CN); Xiaolan Liu, Beijing (CN)

(73) Assignee: GE Precision Healthcare LLC, Waukesha, WI (US)

( * ) Notice: Subject to any disclaimer, the term of this patent is extended or adjusted under 35 U.S.C. 154(b) by 181 days.

(21) Appl. No.: 18/501,898

(22) Filed: Nov. 3, 2023

(65) Prior Publication Data
US 2024/0151788 A1     May 9, 2024

(30) Foreign Application Priority Data

Nov. 4, 2022  (CN) .......................... 202211375551.7

(51) Int. Cl.
   *G01V 3/00*   (2006.01)
   *A61B 5/00*   (2006.01)
   *G01R 33/28*  (2006.01)

(52) U.S. Cl.
   CPC ............ *G01R 33/288* (2013.01); *A61B 5/704* (2013.01); *A61B 5/743* (2013.01)

(58) Field of Classification Search
   CPC .............. G01R 33/287; G01R 33/4835; G01R 33/5608; A61B 2090/374
   USPC ......................................................... 324/309
   See application file for complete search history.

(56) References Cited

U.S. PATENT DOCUMENTS

2019/0209267 A1*  7/2019  Massoels ............. A61C 8/0089

FOREIGN PATENT DOCUMENTS

| CN | 103705262 A | * | 4/2014 | ........... A61N 5/1001 |
| CN | 109965878 A |   | 7/2019 | |

* cited by examiner

*Primary Examiner* — Walter L Lindsay, Jr.
*Assistant Examiner* — Frederick Wenderoth

(57) ABSTRACT

Embodiments of the present invention disclose a magnetic resonance system and a magnetic resonance scanning control method, the method comprising: acquiring a three-dimensional body model of a scan subject; receiving a user operating instruction to mark an implant in the three-dimensional body model of the scan subject to generate a simulated scan subject; acquiring current positioning information of the scan subject on a scanning table, and determining, on the basis of the current positioning information, virtual positioning information of the simulated scan subject in a virtual space, the virtual space comprising distribution information of a spatial field gradient of the magnetic resonance system; and on the basis of the virtual positioning information, evaluating a safety risk related to the spatial field gradient.

10 Claims, 10 Drawing Sheets

MAGNETIC RESONANCE SYSTEM AND MAGNETIC RESONANCE SCANNING CONTROL METHOD

CROSS REFERENCE TO RELATED APPLICATIONS

The present application claims priority and benefit of Chinese Patent Application No. 202211375551.7 filed on Nov. 4, 2022, which is incorporated herein by reference in its entirety.

TECHNICAL FIELD

Embodiments of the present invention generally relate to medical imaging technology, and relate in particular to a magnetic resonance (MR) system and a magnetic resonance scanning control method.

BACKGROUND

When a patient with an implant undergoes magnetic resonance imaging, a strong magnetic field of a magnetic resonance system may cause the implant to be subjected to a strong magnetic force and/or torque, and may thus pose a risk to the patient. A spatial field gradient (SFG) of a static magnetic field B0 is a key parameter in determining relevant risks. The SFG represents the rate of change of the static magnetic field B0 with position. In general, manufacturers of implants will establish an SFG range that the implant products can withstand. Manufacturers of magnetic resonance systems will provide tabular data of maximum SFG values and a two-dimensional contour plot around a magnet, and said pieces of data are generally recorded in operation manuals of the magnetic resonance systems. SFGs at different contour lines are different, and the greater the SFG, the higher the risk factor.

In day-to-day scanning, a technician or physician who helps a patient with magnetic resonance scanning may acquire information of an implant in the patient, estimate a safe positioning location for the patient on a scanning table by means of SFG contour lines in an operation manual, and instruct the patient to position themselves based on the estimated safe positioning location, such that when the scanning table bears the patient and travels along a magnet aperture of the magnetic resonance system, the implant in the patient is in a safe SFG area, preventing a safety incident or hidden danger caused by passing through an area in which the SFG value is too high.

However, considering the anatomy of the patient being scanned, the location of the implant in the patient's body, and the course of the patient's travel with the scanning table in a magnetic resonance system, the physician or technician responsible for the scan must be able to, by relying on experience and visual observation only, accurately apply the SFG values and location mapping provided by the manufacturer to the scan of the implant having known MR scanning conditions in order to be able to determine a safe manner by which to position the patient. The foregoing method causes the physician and the technician to encounter many confusions and challenges in daily decision-making.

SUMMARY

An aspect of the present invention provides a magnetic resonance system and a magnetic resonance scanning control method, the method comprising: acquiring a three-dimensional body model of a scan subject; receiving a user operating instruction to mark an implant in the three-dimensional body model of the scan subject to generate a simulated scan subject; acquiring current positioning information of the scan subject on a scanning table, and determining, on the basis of the current positioning information, virtual positioning information of the simulated scan subject in a virtual space, the virtual space comprising distribution information of a spatial field gradient of a magnetic resonance system; and on the basis of the virtual positioning information, evaluating a safety risk related to the spatial field gradient.

Another aspect of the present invention provides a magnetic resonance scanning control method for a magnetic resonance system, the magnetic resonance system comprising a scanning table and a camera, and the method comprising: acquiring, by means of a camera, a three-dimensional profile image of a scan subject on a scanning table; data-fusing the three-dimensional profile image with a pre-stored standard human model to acquire a three-dimensional body model of the scan subject; displaying the three-dimensional body model of the scan subject, and receiving a user operating instruction to mark an implant in the three-dimensional body model to generate a simulated scan subject; photographing, by means of the camera, the scan subject on the scanning table to acquire current positioning information of the scan subject; disposing the simulated scan subject in a virtual space based on the current positioning information, the virtual space comprising information of a spatial field gradient of the magnetic resonance system, and the simulated scan subject having virtual positioning information in the virtual space; on the basis of the virtual positioning information, evaluating a safety risk related to the spatial field gradient; and determining, on the basis of the evaluation result, whether a magnetic resonance scan can be performed, if yes, then performing a magnetic resonance scan, and if not, then adjusting the positioning of the scan subject, and returning to the step of acquiring the current positioning information of the scan subject.

Another aspect of the present invention provides a magnetic resonance system, including: a magnet assembly formed with a scanning cavity; a scanning table positioned relative to the magnet assembly and traveling in and out of the scanning cavity; and a scanning controller including operating instructions for performing the magnetic resonance scanning control method of any of the above aspects.

BRIEF DESCRIPTION OF THE DRAWINGS

The described and other features, aspects, and advantages of the present invention will be better understood once the following detailed description has been read with reference to the accompanying drawings. In the accompanying drawings, the same reference signs are used to represent the same components throughout the accompanying drawings, in which.

DETAILED DESCRIPTION

Specific embodiments of the present invention will be described in detail below with reference to the accompanying drawings in order to assist those skilled in the art to understand exactly the subject matter set forth in the present invention. In the following detailed description of the following specific embodiments, the present specification does not describe in detail any known functions or configurations to prevent unnecessary details from affecting the disclosure of the present invention.

Unless otherwise defined, the technical or scientific terms used in the claims and the description should be as they are usually understood by those possessing ordinary skill in the technical field to which they belong. Terms such as "first", "second" and similar terms used in the present description and claims do not denote any order, quantity, or importance, but are only intended to distinguish different constituents. The terms "one" or "a/an" and similar terms do not express a limitation of quantity, but rather that at least one is present. The terms "include" or "comprise" and similar words indicate that an element or object preceding the terms "include" or "comprise" encompasses elements or objects and equivalent elements thereof listed after the terms "include" or "comprise", and do not exclude other elements or objects. The terms "connect" or "link" and similar words are not limited to physical or mechanical connections, and are not limited to direct or indirect connections. Furthermore, it should be understood that references to "an embodiment" or "embodiments" of the present disclosure are not intended to be construed as excluding the existence of additional implementations that also incorporate the referenced features.

A "module", "unit", etc., as described herein may be implemented by using software, hardware, or a combination of software and hardware. For example, in accordance with some aspects of the embodiments of the present invention, the "modules" described herein may be implemented as computer program modules or circuit modules.

An "image" described herein may include a displayed image, or may include data that forms the displayed image.

Figure 1:
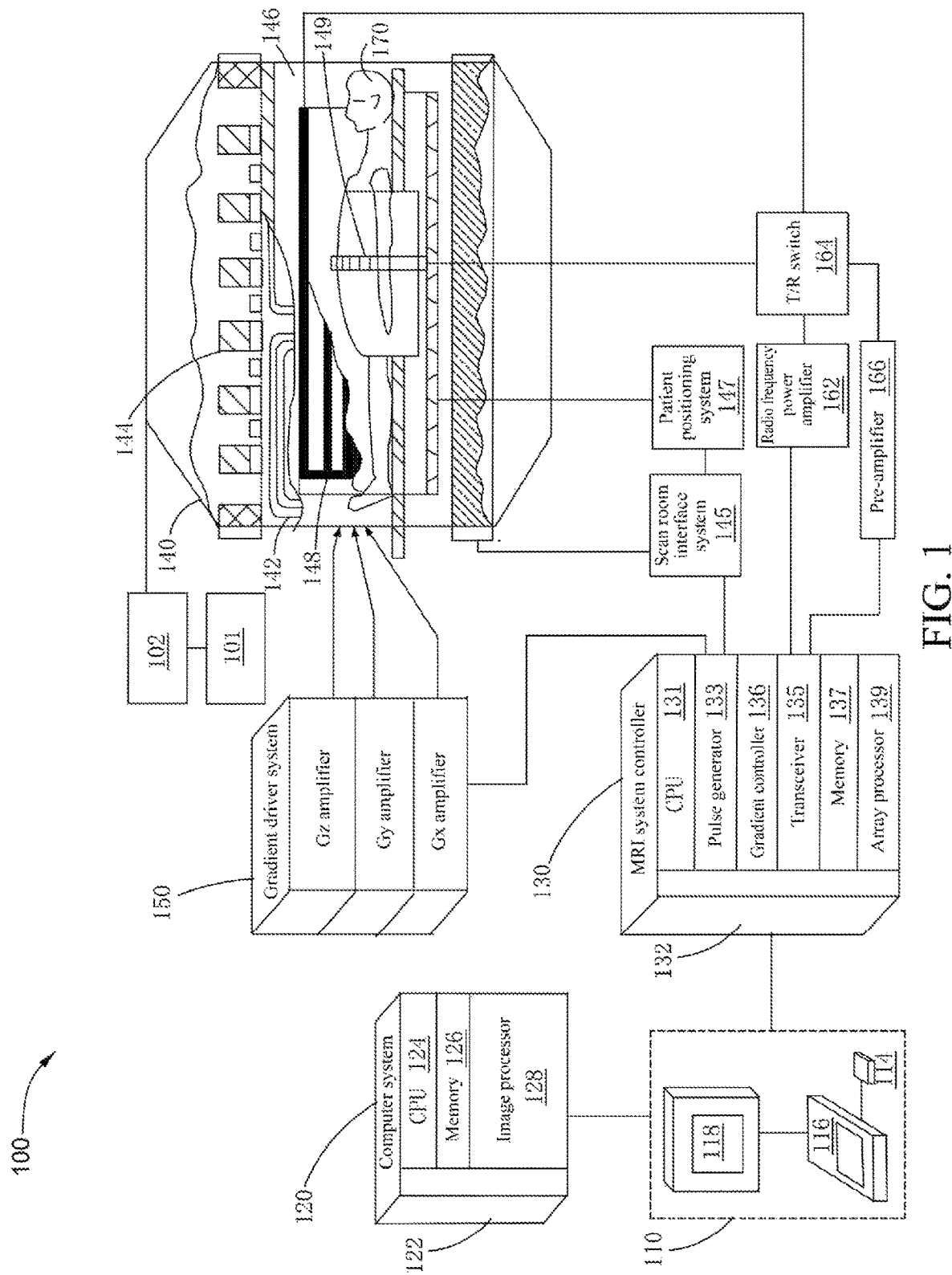
FIG. 1 illustrates an exemplary magnetic resonance (MR) system 100 according to some embodiments of the present invention.

Referring to FIG. 1, an exemplary magnetic resonance (MR) system 100 according to some embodiments of the present invention is illustrated. An operator workstation 110 is used to control the operation of the MR system 100, the operator workstation 110 including an input apparatus 114, a control panel 116, and a display 118. The input apparatus 114 may be a joystick, a keyboard, a mouse, a trackball, a touch-activated screen, voice control, or any similar or equivalent input apparatus. The control panel 116 may include a keyboard, a touch-activated screen, voice control, a button, a slider, or any similar or equivalent control apparatus. The operator workstation 110 is coupled to and communicates with a computer system 120, and provides an interface to allow an operator to plan a magnetic resonance scan, display an image, perform image processing, and store data and images.

The computer system 120 includes a plurality of modules that communicate with one another by means of an electrical and/or data connection module 122. The connection module 122 may be a wired communication link, an optical fiber communication link, a wireless communication link, and the like. The computer system 120 may include a central processing unit (CPU) 124, a memory 126, and an image processor 128. In some embodiments, the image processor 128 may be replaced by an image processing function run in the CPU 124. The computer system 120 may be connected to an archive media apparatus, a persistent or backup memory, or a network. The computer system 120 may be coupled to and communicates with a separate MR system controller 130.

The MR system controller 130 includes a set of modules that communicate with one another by means of an electrical and/or data connection module 132. The connection module 132 may be a direct wired communication link, an optical fiber communication link, a wireless communication link, and the like. In an alternative embodiment, modules of the computer system 120 and the MR system controller 130 may be implemented on the same computer system or on a plurality of computer systems. The MR system controller 130 may include a CPU 131, a sequence pulse generator 133 that communicates with the operator workstation 110, a transceiver (or an RF transceiver) 135, a gradient controller 136, a memory 137, and an array processor 139.

A subject 170 of the MR scan may be positioned within a cylindrical imaging volume 146 of a magnetic resonance assembly 140 by means of a scanning table. The MR system controller 130 controls the scanning table to travel in a Z-axis direction of the magnetic resonance system so as to transport the subject 170 into the imaging volume 146. The magnetic resonance assembly 140 includes a superconducting magnet having a superconducting coil 144, a radio frequency (RF) coil assembly, and a gradient coil assembly 142. The superconducting coil 144 has a magnet aperture to form the cylindrical imaging volume. During operation, the superconducting coil 144 provides a static uniform longitudinal magnetic field $B_0$ throughout the cylindrical imaging volume 146. The radio frequency coil assembly may include a body coil 148 and a surface coil 149, and may be used to send and/or receive a radio frequency signal.

The MR system controller 130 may receive a command from the operator workstation 110 to indicate an MRI scan sequence that is to be executed during the MRI scan. The "scan sequence" above refers to a combination of pulses that have specific intensities, shapes, time sequences, and the like and that are applied when a magnetic resonance imaging scan is executed. The pulses may typically include, for example, a radio frequency pulse and a gradient pulse. A plurality of scan sequences may be pre-stored in the computer system 120, so that a sequence suitable for clinical examination requirements can be indicated by means of the operator workstation. The clinical examination requirements may include, for example, an imaging site, an imaging function, an imaging effect, scanning safety and the like. The sequence pulse generator 133 of the MR system controller 130 sends, on the basis of the indicated sequence, an instruction describing the time sequences, intensities, and shapes of the radio frequency pulse and gradient pulse in the sequence so as to operate a system component that executes the sequence.

The radio frequency pulse in the scan sequence sent by the sequence pulse generator 133 may be generated by the transceiver 135, and the radio frequency pulse is amplified by a radio frequency power amplifier 162. When a toggle switch 141 is toggled to the body coil 148, the amplified radio frequency pulse is provided to the body coil 148 by means of a transmit/receive switch (T/R switch) 164, and the RF body coil 148 then provides a transverse magnetic field $B_1$. The transverse magnetic field $B_1$ is substantially perpendicular to $B_0$ throughout the entire cylindrical imaging volume 146. The transverse magnetic field $B_1$ is used to excite stimulated nuclei in the body of the scan subject so as to generate an MR signal.

The gradient pulse in the scan sequence sent by the sequence pulse generator 133 may be generated by means of the gradient controller 136 and acts on a gradient driver 150. The gradient driver 150 includes $G_x$, $G_y$, and $G_z$ amplifiers, and the like. Each of the $G_x$, $G_y$, and $G_z$ gradient amplifiers is used to excite a corresponding gradient coil in the gradient coil assembly 142, so as to generate a magnetic field gradient used to spatially encode an MR signal during an MR scan.

The sequence pulse generator 133 is coupled to and communicates with a scan room interface system 145, and the scan room interface system 145 receives signals from various sensors associated with the state of the magnetic resonance assembly 140 and various processors provided in a scan room. The scan room interface system 145 is further coupled to and communicates with a patient positioning system 147, the patient positioning system 147 sending and receiving a signal to control the scanning table to travel so as to transport the patient or the subject 170 to a desired position to perform the MR scan.

As described above, the RF body coil 148 and the RF surface coil 149 may be used to transmit a radio frequency pulse and/or receive MR signals from the scan subject. The MR signals emitted by excited nuclei in the body of the scan subject may be sensed and received by the RF body coil 148 or the RF surface coil 149 and then sent back to a pre-amplifier 166 by means of the T/R switch 164. The T/R switch 164 may be controlled by a signal from the MR system controller 130 to electrically connect, during a transmit mode, the radio frequency power amplifier 162 to the RF body coil 148 and to connect, during a receive mode, the pre-amplifier 166 to the RF body coil 148. The T/R switch 164 may further enable the RF surface coil 149 to be used in the transmit mode or the receive mode.

In some embodiments, the MR signals sensed and received by the RF body coil 148 or the RF surface coil 149 and amplified by the pre-amplifier 166 are demodulated, filtered, and digitized in a receiving portion of the transceiver 135, and transmitted as a raw k-space data array to the memory 137 in the MR system controller 130.

A reconstructed magnetic resonance image may be obtained by transforming/processing the stored raw k-space data. For each image to be reconstructed, the data is rearranged into separate k-space data arrays, and each of said separate k-space data arrays is inputted to the array processor 139, the array processor being operated to transform the data into an array of image data by Fourier transform.

The array processor 139 uses transform methods, most commonly Fourier transform, to create images from the received MR signals. These images are transmitted to the computer system 120 and stored in the memory 126. In response to commands received from the operator workstation 110, the image data may be stored in a long-term memory, or may be further processed by the image processor 128 and transmitted to the operator workstation 110 for presentation on the display 118.

In various embodiments, components of the computer system 120 and MR system controller 130 may be implemented on the same computer system or on a plurality of computer systems. It should be understood that the MR system 100 shown in FIG. 1 is intended for illustration. Suitable MR systems may include more, fewer, and/or different components.

The MR system controller 130 and the image processor 128 may separately or collectively include a computer processor and a storage medium. The storage medium records a program for predetermined data processing that is to be executed by the computer processor. For example, the storage medium may store a program used to implement scanning processing (such as a scan flow and an imaging sequence), image reconstruction, image processing, and the like. Specifically, the storage medium may store the magnetic resonance scanning control method of any of the embodiments of the present invention. The described storage medium may include, for example, a ROM, a floppy disk, a hard disk, an optical disk, a magneto-optical disk, a CD-ROM, or a non-volatile memory card.

As described above, the superconducting coil 144 provides a longitudinal magnetic field $B_0$ during operation. However, the longitudinal magnetic field is relatively uniform only within a certain range (e.g., FOV) close to the center of the magnet. Outside this range, the field intensity of the longitudinal magnetic field $B_0$ may vary with position, and the change rate of the field intensity at different positions is different, which may be described by means of a spatial field gradient (SFG).

Figure 2:
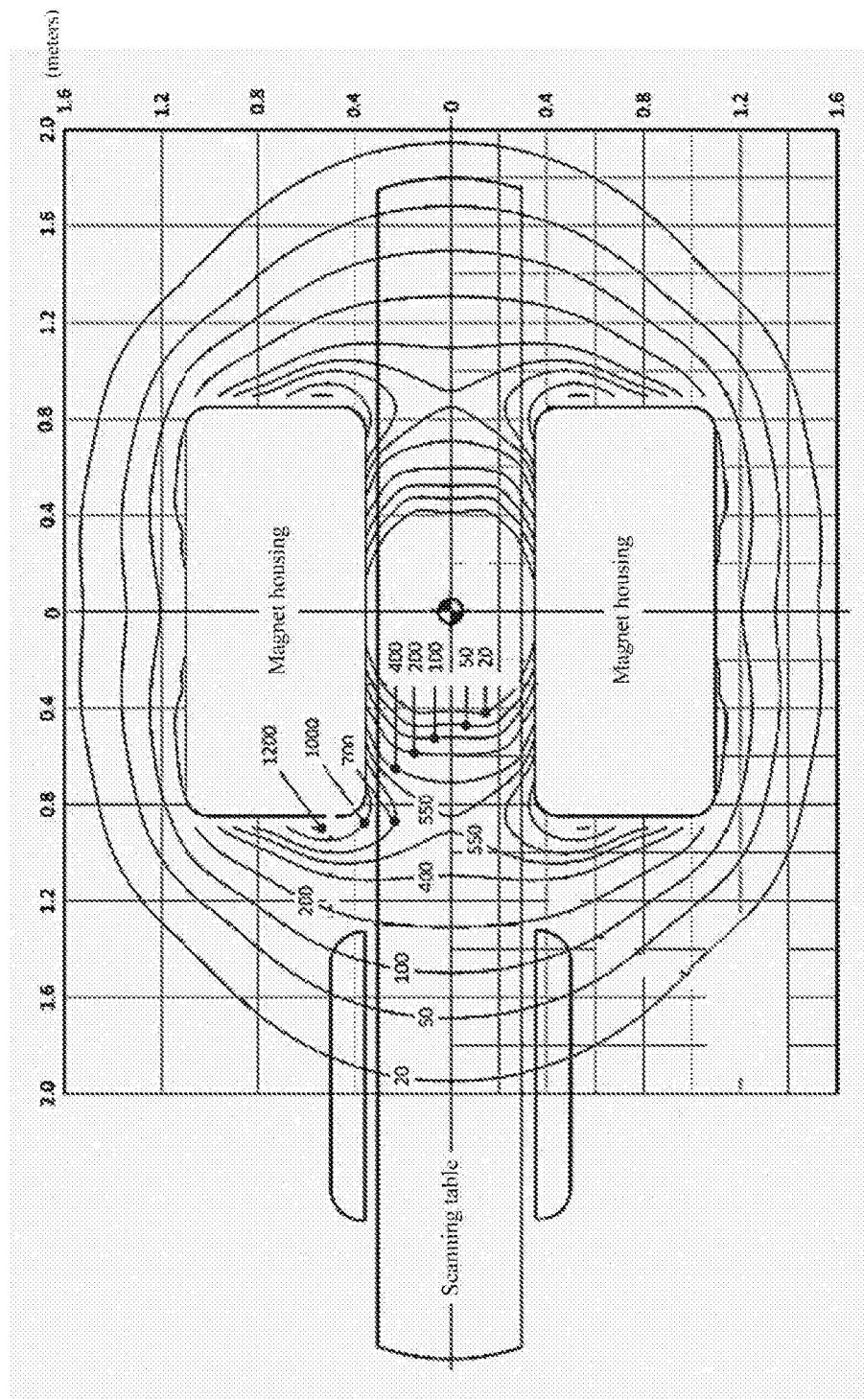
FIG. 2 illustrates an example of an SFG two-dimensional contour plot of the magnetic resonance system.

As shown in FIG. 2, an example of an SFG two-dimensional contour plot of a magnetic resonance system is shown, wherein a plurality of contour lines having a spatial field gradient value of 20, 50, 100, 400, 550, 700, 1000, 1200 (the unit being Gauss/centimeter), etc., are shown. Some implants may not be allowed to pass through the contour line of 550 Gauss/centimeter, while some implants may be limited to lower SFG values, for example, 400 Gauss/centimeter or lower, and therefore there may be different possibilities based on different implant categories. The implant described above may include a stent, a pacemaker, a steel pin, a screw, and the like.

FIG. 2 also exemplarily illustrates a scanning table, which is used for carrying a scan subject (e.g., a patient). An implant may exist in one or more body parts of the scan subject. A physician or technician may need to perform a spatial prediction by combining a two-dimensional contour plot and the location of the implant in the patient's body, so as to determine that the current positioning method for the patient can avoid the implant passing through a limited SFG value area during traveling, for example, an area having an SFG value of 400 Gauss/centimeter. Such a prediction is not intuitive enough, and may lead to safety problems caused by improper positioning.

With continued reference to FIG. 1, in embodiments of the present invention, a scanning controller 101 is provided for controlling the magnetic resonance system to perform the magnetic resonance scanning control method of the present invention, so as to intuitively indicate how to perform a scan subject positioning operation in order to avoid safety problems caused by the implant being affected by the main magnetic field space gradient. In some embodiments, the scanning controller 101 may be integrated in the MR system controller 130 or the computer system 120, or may be independently provided.

In embodiments of the present invention, a three-dimensional image acquisition device 102 may also be provided for acquiring a three-dimensional profile image of the scan subject positioned on the scanning table. The three-dimensional profile image may be utilized by the scanning controller 101 to acquire a three-dimensional body model of the scan subject to mark the implant in the three-dimensional body model, and then to perform a positioning indication based on the three-dimensional body model marked with the implant, which will be described in detail below.

In one embodiment, the three-dimensional image acquisition device 102 may include hardware devices, such as a camera, a TOF (time-of-flight) sensor, a laser scanner, etc., disposed on a magnetic resonance assembly housing (or a magnet housing), wherein the camera may include a depth video camera or a two-dimensional video camera. In other embodiments, the three-dimensional image acquisition device 102 may include a data processing module, which may generate the above-described three-dimensional profile image of the scan subject based on physiological information of the scan subject inputted by a user. In some embodiments, the data processing module may be a deep learning network or other data processing models.

Figure 3:
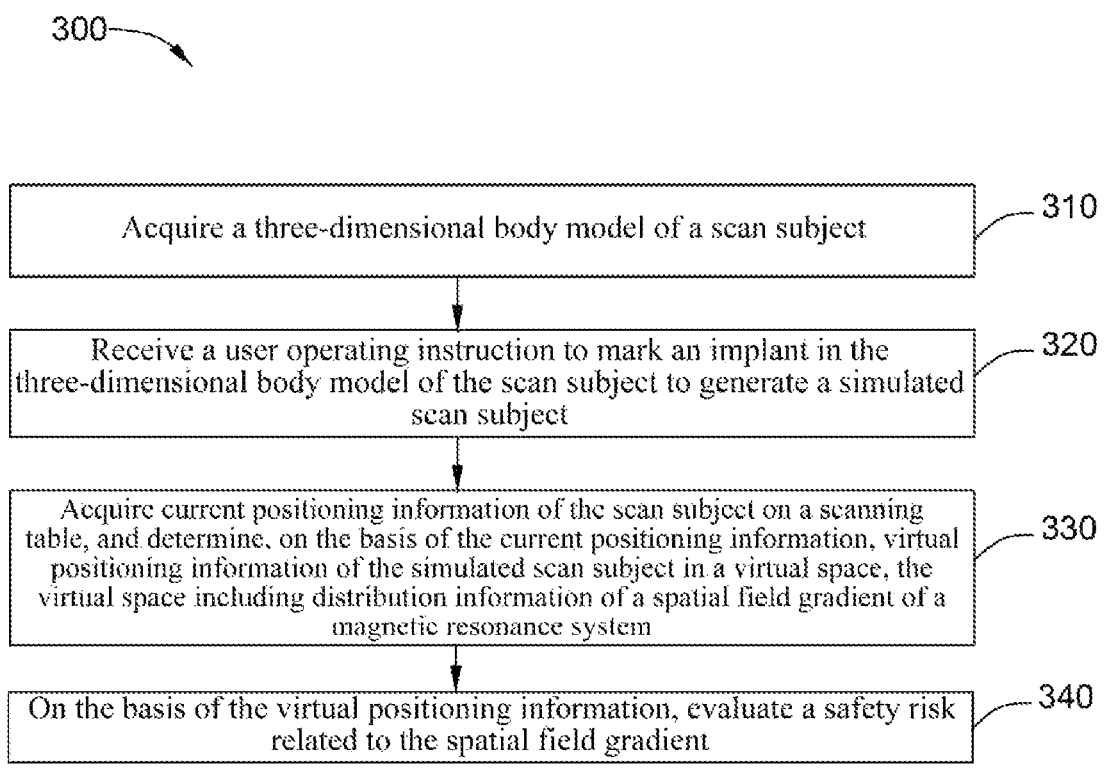
FIG. 3 illustrates a flowchart 300 of a magnetic resonance scanning control method according to an embodiment of the present invention.

With reference to FIG. 3, a flowchart of a magnetic resonance scanning control method 300 according to an embodiment of the present invention is shown. In the method, in step 310, a three-dimensional body model of a scan subject is acquired, the three-dimensional body model including at least one body organ. The "three-dimensional body model of the scan subject" described in the present step may vary depending on any among the identity, age, height, weight, body proportion, appearance feature, etc., of the scan subject. In some embodiments, the three-dimensional body model may include at least one human organ, for example, may include but is not limited to, the brain, heart, liver, spleen, stomach, etc. In some other embodiments, the three-dimensional body model may also include only a three-dimensional profile of the body, and a physician may determine positions of different body parts in the three-dimensional profile according to the basic human structure.

Figure 4:
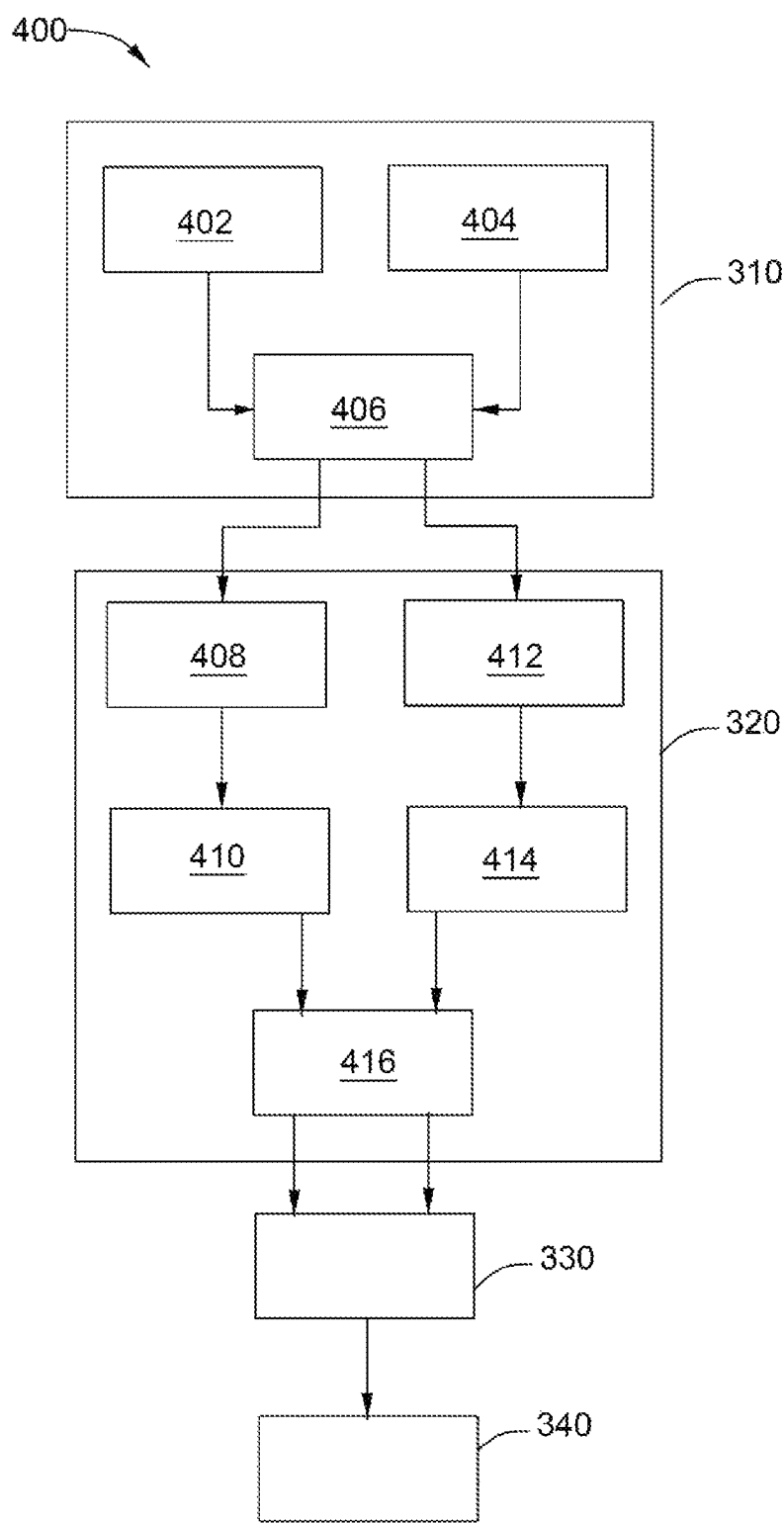
FIG. 4 illustrates a flowchart 400 of a magnetic resonance scanning control method according to another embodiment of the present invention.

FIG. 4 illustrates a flowchart 400 of a magnetic resonance scanning control method according to another embodiment of the present invention, wherein sub-steps of some of the steps in FIG. 3 are more specifically shown. As shown in FIG. 4, step 310 may specifically include step 402 or 404. In step 402, three-dimensional profile information of the scan subject is acquired. For example, a scan subject positioned on a scanning table may be photographed by means of a camera to acquire a three-dimensional profile image of the scan subject. The camera may, for example, be a depth video camera. Optionally, the camera may also include a two-dimensional video camera, and the three-dimensional profile image may be obtained based on a two-dimensional image taken by the two-dimensional video camera, for example, by means of image processing. By means of the camera, a current image of the scan subject may be obtained more accurately and in real time, such that a simulated scan subject that better matches with the real scan subject can be subsequently generated based on the three-dimensional profile image. The camera can also be used to subsequently perform real-time photographing the scan subject to obtain current positioning information thereof or real-time positioning information, which facilitates simulating a more realistic positioning scenario for risk evaluation.

In other embodiments, the three-dimensional profile image and the current positioning information of the scan subject may also be acquired by means of, for example, a time-of-flight (TOF) sensor, a laser scanner, or other apparatuses.

In other embodiments, the three-dimensional profile information of the scan subject may also be obtained by means of image generation instead of actual photographing. For example, at least one among the physiological information of the scan subject and the two-dimensional image of the scan subject may be data-processed by means of a data processing model, to acquire the three-dimensional profile image of the scan subject.

For example, when sufficient training samples and priori knowledge are acquired, the data processing model may include a deep learning network, and the deep learning network may be utilized to obtain the three-dimensional profile information of the scan subject. Specifically, in step 404, at least one among the physiological information of the scan subject and the two-dimensional image of the scan subject may be inputted into a pre-trained deep learning network, to acquire the three-dimensional profile image of the scan subject.

The data processing model may also utilize other preset algorithms to acquire the three-dimensional profile image of the scan subject.

The physiological information may include but is not limited to, the age, gender, height, weight, etc., of the scan subject. The two-dimensional image may be collected before performing a magnetic resonance scan on the scan subject, or may be an image taken on site by using an existing two-dimensional photography apparatus. Since, in existing diagnosis and treatment processes, the system may acquire the physiological information of a patient by means of a variety of approaches when performing medical image inspection on the patient, the acquired physiological information or two-dimensional image is thus used to generate the three-dimensional profile image of the scan subject, which does not require adding new hardware apparatuses or changing the system structure, and is easy to implement.

The three-dimensional profile image of the scan subject obtained in step 402 or 404 may be used to further operate to acquire a three-dimensional body model that includes human organs and the anatomy of which matches that of a real scan subject, which will be described in step 406.

In step 406, the three-dimensional profile image is data fused with a pre-stored standard human model to acquire the three-dimensional body model of the scan subject, wherein the standard human model includes at least one human organ. The standard human model may include a plurality of models, which may be based on different ages, genders, body types, etc., respectively.

By performing the described data fusion, the obtained three-dimensional body model not only has a conventional human anatomy, but may also be individually varied based on different individuals, such that the same is close enough to the anatomical structure of the real scan subject, which facilitates subsequent proper implant marking and safety risk evaluation.

Furthermore, the three-dimensional profile image of the scan subject and the standard human model may be matched based on preset weight information of different body parts. In this way, it is avoided that the same proportion is simply used to make variations and matches on all body parts, enabling the obtained model to be closer to reality. For example, for an obese scan subject, compared with the standard model, changes to the limbs are larger, while changes to the heart are smaller. Therefore, the weight of the limbs may be larger, and the weight of the heart may be smaller.

With continued reference to FIG. 3, step 320 includes marking, wherein a user operating instruction is received to mark an implant in the three-dimensional body model of the scan subject to generate a simulated scan subject. The "user" may include the physician or the technician described above, who may mark the implant in the three-dimensional body model by means of the operator workstation 110. The above-described three-dimensional body model obtained in step 310 and a graphical user interface for marking may be displayed by means of the display 118.

As shown in FIG. 4, a step of marking 320 may include step 408 and step 410. In step 408, basic information of the implant of the scan subject is received, and in step 410, the implant is automatically marked in the three-dimensional body model of the scan subject based on the basic information of the implant. The basic information of the implant may include one or more among implantation location information (e.g., a body part), the size of the implant, and a safety parameter range of the implant. The implantation location information may be related to the function or location of the implant. For example, a cardiac pacemaker, a cardiac stent, etc., may be related to the heart, and a nerve stimulator may be related to the brain, or other locations of the body. The safety parameter range may include the range of spatial field gradient that can be withstood, which may be defined by the manufacturer of the implant and obtained or inputted by means of the magnetic resonance system.

The basic information of the implant may be received in a variety of ways, for example, may be manually inputted by the user, or may be automatically acquired by the system based on a historical scan record of the scan subject, or may be obtained from an electronic medical record of the scan subject based on a network-interconnected medical institution or medical apparatus.

In step 408, a graphical user interface may be provided for the operator to input or select the basic information of the implant. In one example of step 410, when it is determined that the implant should be disposed in the heart based on the inputted basic information, the scanning controller then automatically configures an implant identifier in the vicinity of the heart. In step 410, the three-dimensional body model and the implant marked therein may be displayed, and a dynamic interface for automatically marking the implant in the three-dimensional body model may also be displayed.

As shown in FIG. 4, in another optional embodiment, step 320 may include step 412 and step 414. In step 412, the three-dimensional body model of the scan subject is displayed on the graphical user interface. In step 414, an operational input of a user on the graphical user interface is received to add an implant identifier in the three-dimensional body model. In this way, the understanding of the implant of the scan subject can allow the operator to more flexibly mark the implant, so as to be closer to reality. However, the implant identifier may be used to represent the implant, but not necessarily the same as the real implant profile.

Figure 5:
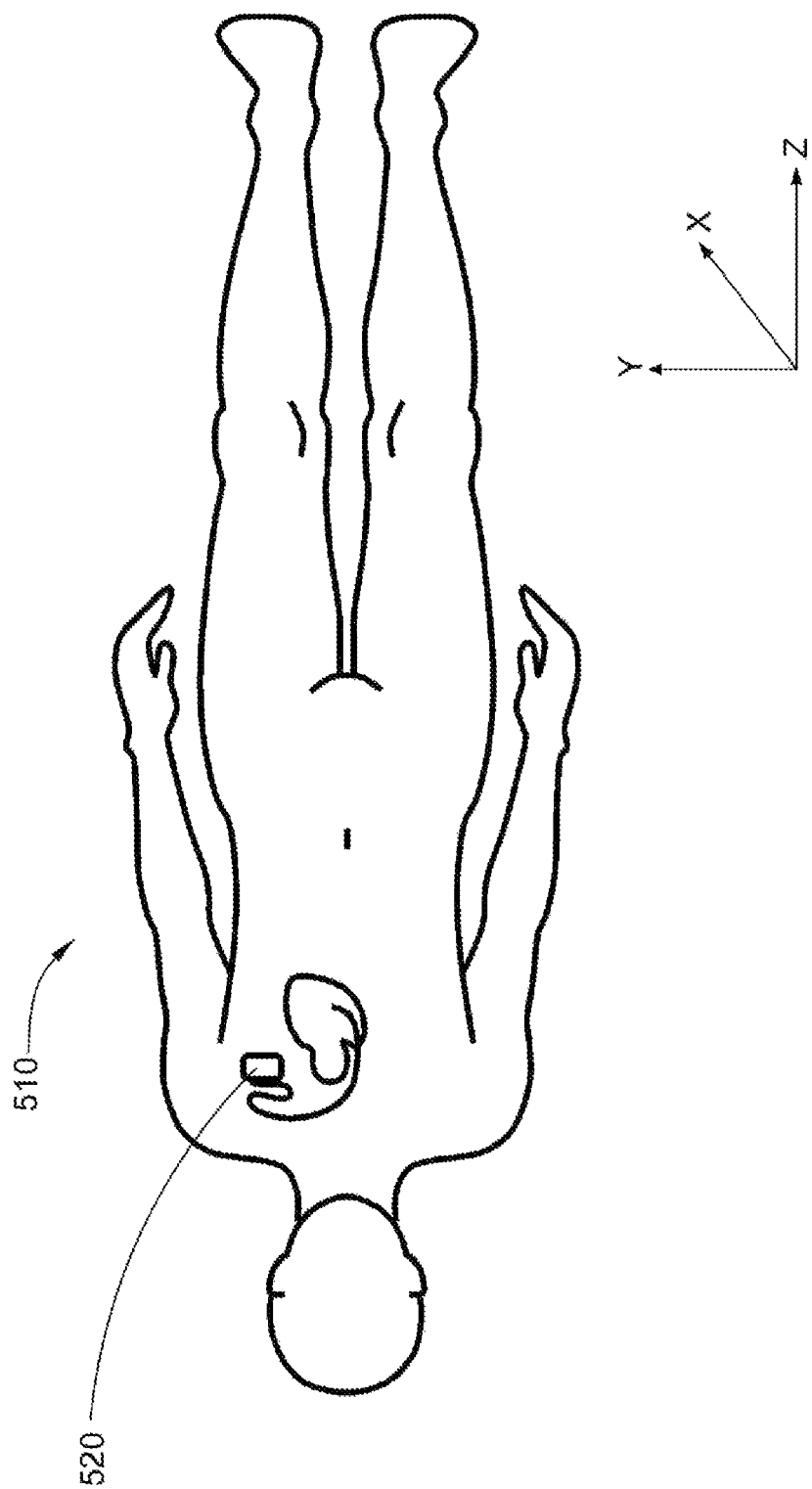
FIG. 5 illustrates an example interface for marking an implant in a three-dimensional body model of a scan subject in a three-dimensional coordinate system in embodiments of the present invention.

Specifically, in step 414, the three-dimensional body model may be displayed in whole on the graphical user interface, and the operator may make a mark at a corresponding location in the three-dimensional volume. An example of such a marked interface may be shown in FIG. 5, in which the entirety of a stereoscopic three-dimensional body model 510 is shown, and an implant identifier 520 is disposed at one time in a stereoscopic space of the model 510.

Figure 6:
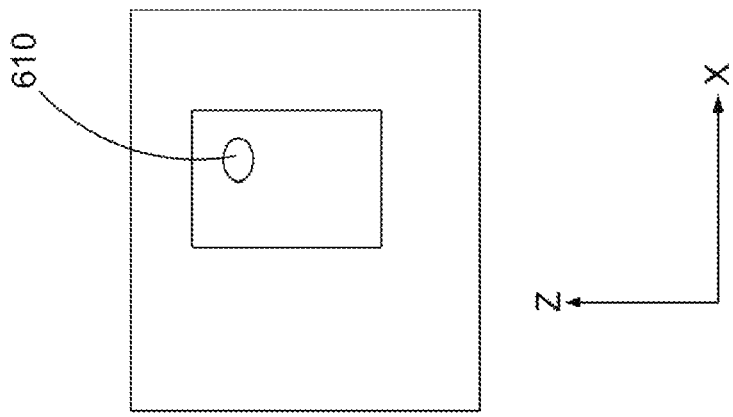
FIG. 6 illustrates an example interface for marking an implant in a three-dimensional body model of a scan subject in a two-dimensional coordinate system in embodiments of the present invention.
Figure 6:
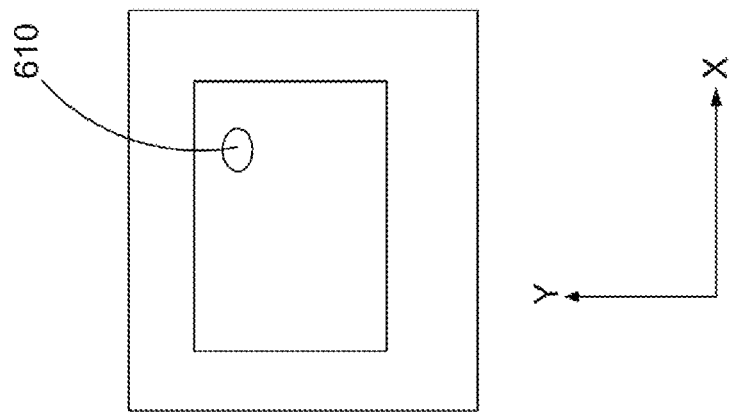
Figure 6:
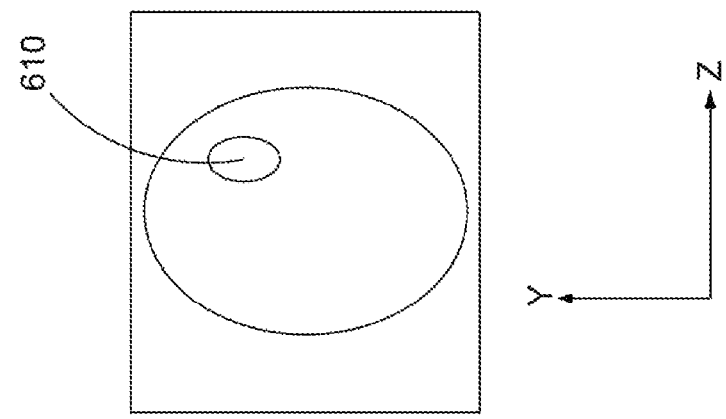

In other implementations, a plurality of two-dimensional planes of the three-dimensional body model may be displayed on a plurality of graphical user interfaces or on a plurality of regions of one graphical user interface, respectively. The plurality of two-dimensional planes may be disposed based on anatomical planes of the human anatomy, for example, three two-dimensional planes may be disposed along coronal, sagittal, and axial positions of the human body, respectively. Such a two-dimensional interface may act as an auxiliary interface for the marking interface or directly as the marking interface, such that the operator may make a mark according to the position of the implant on each two-dimensional plane. FIG. 6 illustrates examples of a plurality of two-dimensional planes for marking, including three orthogonal two-dimensional planes X-Y, Y-Z, and X-Z, wherein each two-dimensional plane may be one anatomical plane of the three-dimensional body model of the scan subject, and an implant identifier 610 is located at a corresponding location of each plane. FIG. 6 illustrates a schematic diagram of a two-dimensional plane as a stand-alone marking interface. However, such an interface may be combined with the interface shown in FIG. 5 so as to assist one another. FIG. 6 only schematically illustrates a two-dimensional plan view of a simple graphic. However, a person skilled in the art may understand that in the embodiments of the present invention, the two-dimensional plane includes an anatomical plane of the human body.

As shown in FIG. 4, the implant marked in the three-dimensional body model in any of the above-described manners may be further adjusted, which may be performed by means of step 416, in which at least one among translating, scaling, and rotating operations is performed on the marked implant of the three-dimensional body model in at least one two-dimensional coordinate system.

In one example, when the three-dimensional body model and the implant therein are displayed stereoscopically as a whole in a three-dimensional coordinate system X-Y-Z, any one among the X-Y, X-Z, and Y-Z planes may be locked to adjust the location, profile, and pose of the implant therein.

In another example, when the three-dimensional body model and the implant therein are displayed as cross-sections in a two-dimensional coordinate system, the location, profile, and pose of the implant may be chosen to be adjusted in either coordinate system.

After the corresponding implant identifier is marked in the three-dimensional body model of the scan subject based on the real implant in the body of the scan subject, a simulated scan subject that simulates the real scan subject is formed.

With continued reference to FIG. 3, in step 330, current positioning information of the scan subject on the scanning table is acquired, and virtual positioning information of the simulated scan subject in a virtual space is determined based on the current positioning information, the virtual space including distribution information of a spatial field gradient of the magnetic resonance system. Specifically, the virtual space may be used to simulate a magnetic field space of a real main magnet, and thus the distribution information of the spatial field gradient therein is also consistent with information of a real spatial field gradient.

The "current positioning information" is actual positioning information of the scan subject on the scanning table before one instance of risk evaluation is performed, which may be positioning information monitored in real time. For example, the current positioning information of the scan subject on the scanning table may be acquired by real-time photographing the scanning table of the magnetic resonance system and the scan subject positioned on the scanning table. The apparatus for the real-time photographing may be a two-dimensional photography apparatus or a three-dimensional photography apparatus, or may be a depth video camera, a TOF sensor, or other stereoscopic video cameras, for acquiring the three-dimensional profile image of the scan subject in step 402. In this step, the location, pose, etc. of the simulated scan subject on the scanning table may be determined based on the location, pose, etc. of the scan subject on the scanning table which is monitored in real time, so as to simulate a real positioning scenario, to acquire the virtual positioning information.

The "current positioning information" may also be default positioning information according to a customary positioning manner. For example, it is generally considered that the body center in the height direction of the scan subject is habitually positioned in the center of the scanning table extending in a Z direction, and the head of the scan subject is usually habitually positioned in a region of the top portion of the scanning table. Based on such positioning habits, and in combination with the obtained simulated scan subject, the virtual positioning information of the simulated scan subject in the virtual space may be determined.

Figure 7:
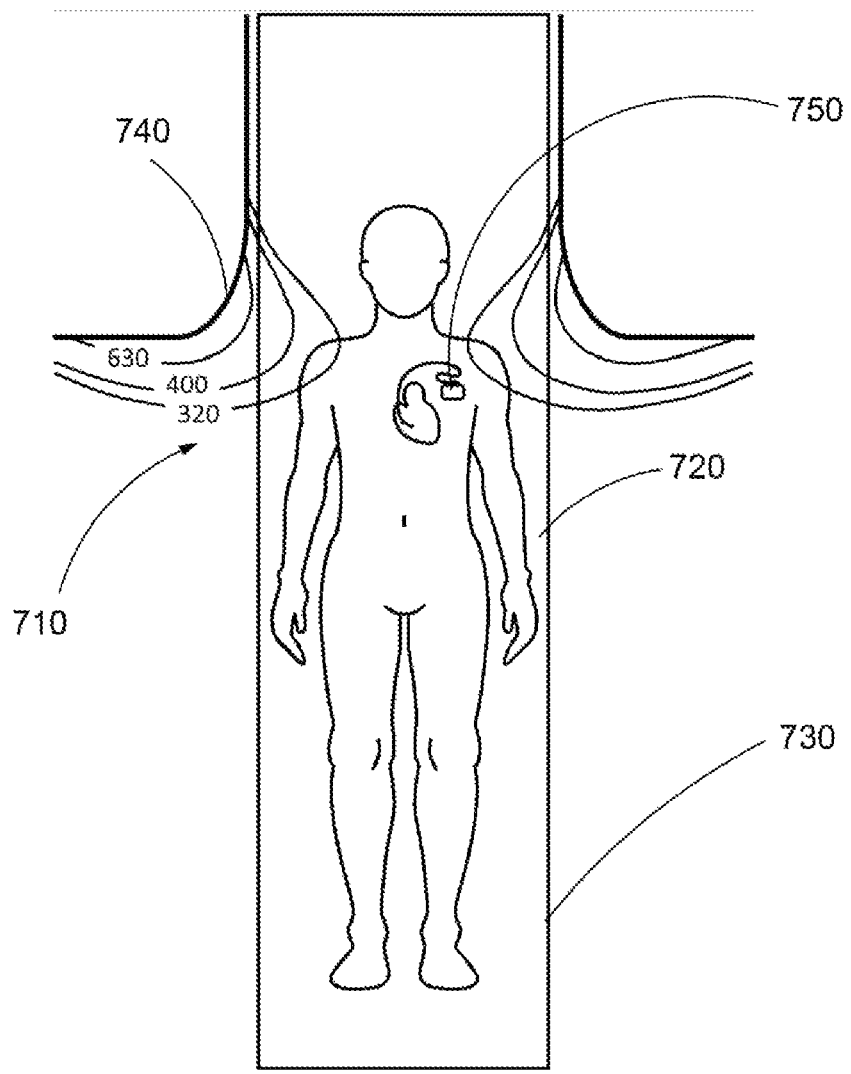
FIG. 7 illustrates an example of a virtual space and a simulated scan subject located in the space in embodiments of the present invention.

In embodiments of the present invention, the virtual positioning information may be displayed to facilitate the observation of the operator. For example, the simulated scan subject and contour lines of the spatial field gradient in the virtual space in which the same is located may be displayed. As shown in FIG. 7, an example of a virtual space 710 and a simulated scan subject 720 located in the space is shown. The simulated scan subject 720 is positioned on a scanning table 730 (which may be a real image of a scanning table, or may be a scanning table simulated based on a real image), as shown in FIG. 7, and contour lines 740 of a spatial field gradient are included in the virtual space 710. While FIG. 7 only schematically illustrates a two-dimensional image, it can be understood that both the virtual space 710 and the simulated scan subject 720 therein are three-dimensional volumes having depth information, and therefore when a risk evaluation is performed, it can be predicted not only whether the implant passes through a spatial field gradient on a surface of the scanning table, but also whether the same passes through a spatial field gradient in the depth direction.

With continued reference to FIG. 4, in step 340, a safety risk related to the spatial field gradient may be evaluated based on the virtual positioning information. For example, the spatial field gradient that the implant in the scan subject will pass during traveling of the scan subject may be estimated based on the location information of the marked implant 750 in the simulated scan subject 720 and the virtual positioning information. Specifically, the range of travel of the scanning table of the magnetic resonance system may be acquired according to a scanning protocol that has been determined. Which contour lines 740 the implant 750 of the simulated scan subject 720 will pass when the scanning table travels in the range of travel are predicted, and if the spatial field gradient value of the contour line that is passed is above a nominal limited value of the implant, it will be considered that there is a safety risk associated with the spatial field gradient.

Figure 8:
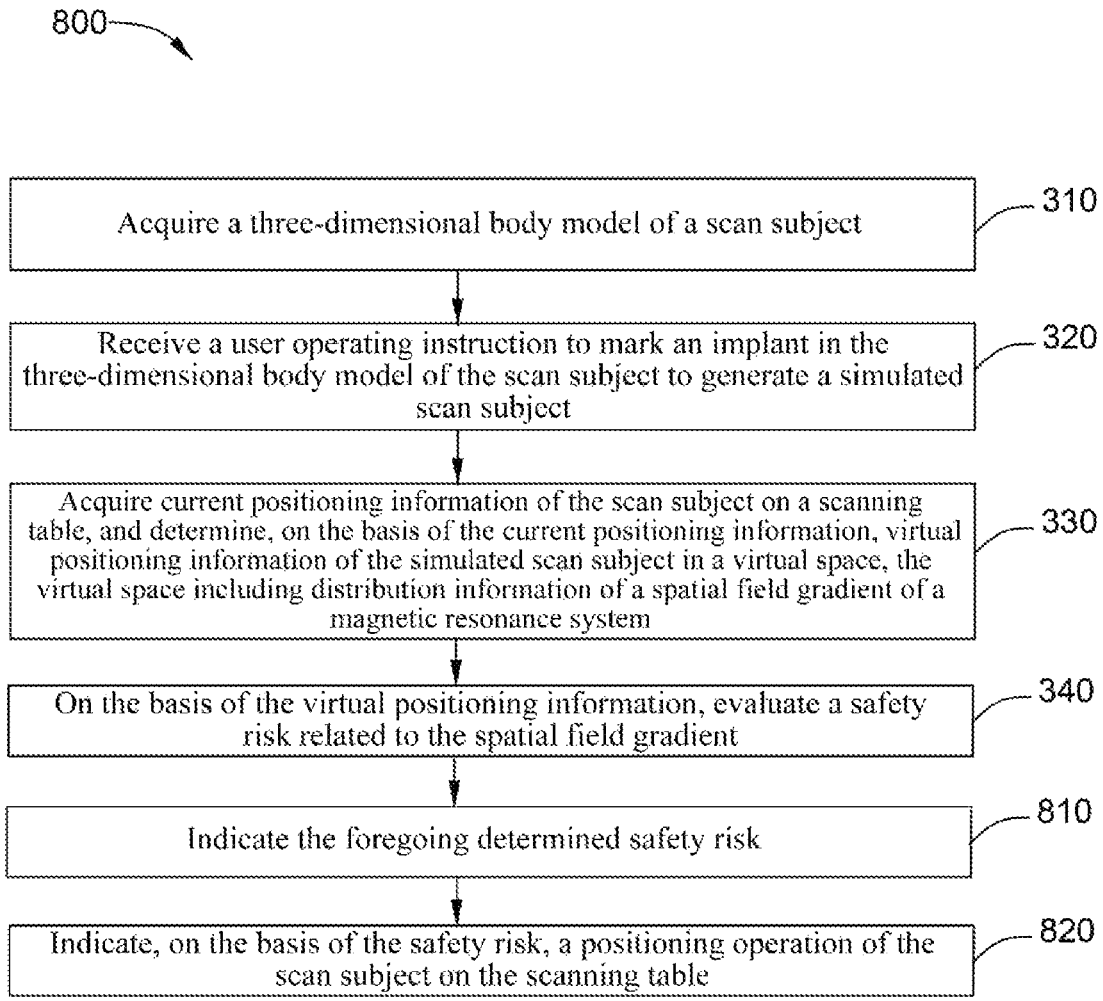
FIG. 8 illustrates a flowchart 800 of a magnetic resonance scanning control method according to another embodiment of the present invention.

With reference to FIG. 8, the scanning control method of the present invention may further include step 810, wherein the above-determined safety risk is indicated. The indication may be implemented by means of at least one among voice, image display, text display, light, etc. Specific risk content may be indicated to the operator. For example, which contour line the implant is likely to pass when the scanning table travels is indicated.

The scanning control method may further include step 820, in which a positioning operation of the scan subject on the scanning table is indicated based on the above-determined safety risk. The indication may be implemented by means of at least one among voice, image display, text display, light, etc. It may be indicated to the operator how to adjust the positioning of the scan subject in order to avoid said safety risk. For example, the position, direction, or distance of movement of the scan subject may be suggested, or an adjustment of the pose of the scan subject may also be suggested.

Figure 9:
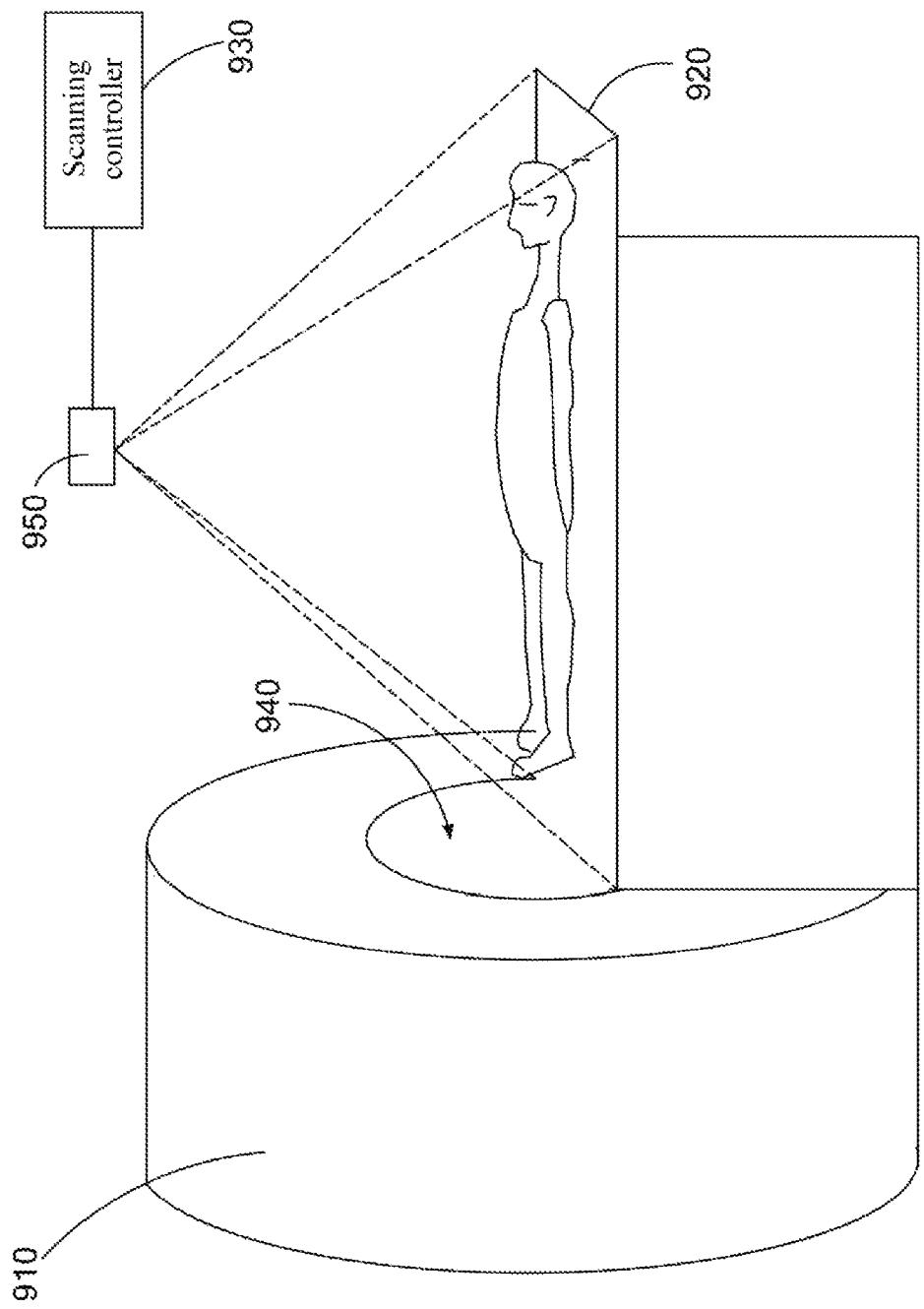
FIG. 9 illustrates a schematic diagram of a magnetic resonance system according to another embodiment of the present invention.

FIG. 9 illustrates an example of a magnetic resonance system of the present invention, which may include at least some of the components in the system 100 shown in FIG. 1, and in particular, the magnetic resonance system may include a magnet assembly 910, a scanning table 920, and a scanning controller 930. The magnet assembly 910 is formed with a scanning cavity 940, and the scanning table 920 is positioned relative to the magnet assembly 910 and travels in and out of the scanning cavity.

The magnetic resonance system further includes a camera 950, which may be positioned relative to the scanning table 920 such that a scan subject located on the scanning table 920 can be photographed. Specifically, the camera 950 may be mounted on the magnetic resonance assembly 910 and located above the scanning table 920. In some embodiments, the camera 950 may be secured on the magnetic resonance assembly 910 by means of a support 960.

The camera 950 is used to acquire three-dimensional profile information of the scan subject. The three-dimensional profile information may be transmitted to the scanning controller 930 to be used to predict safety risks, and the scan subject is further positioned based on the predicted safety risks.

Figure 10:
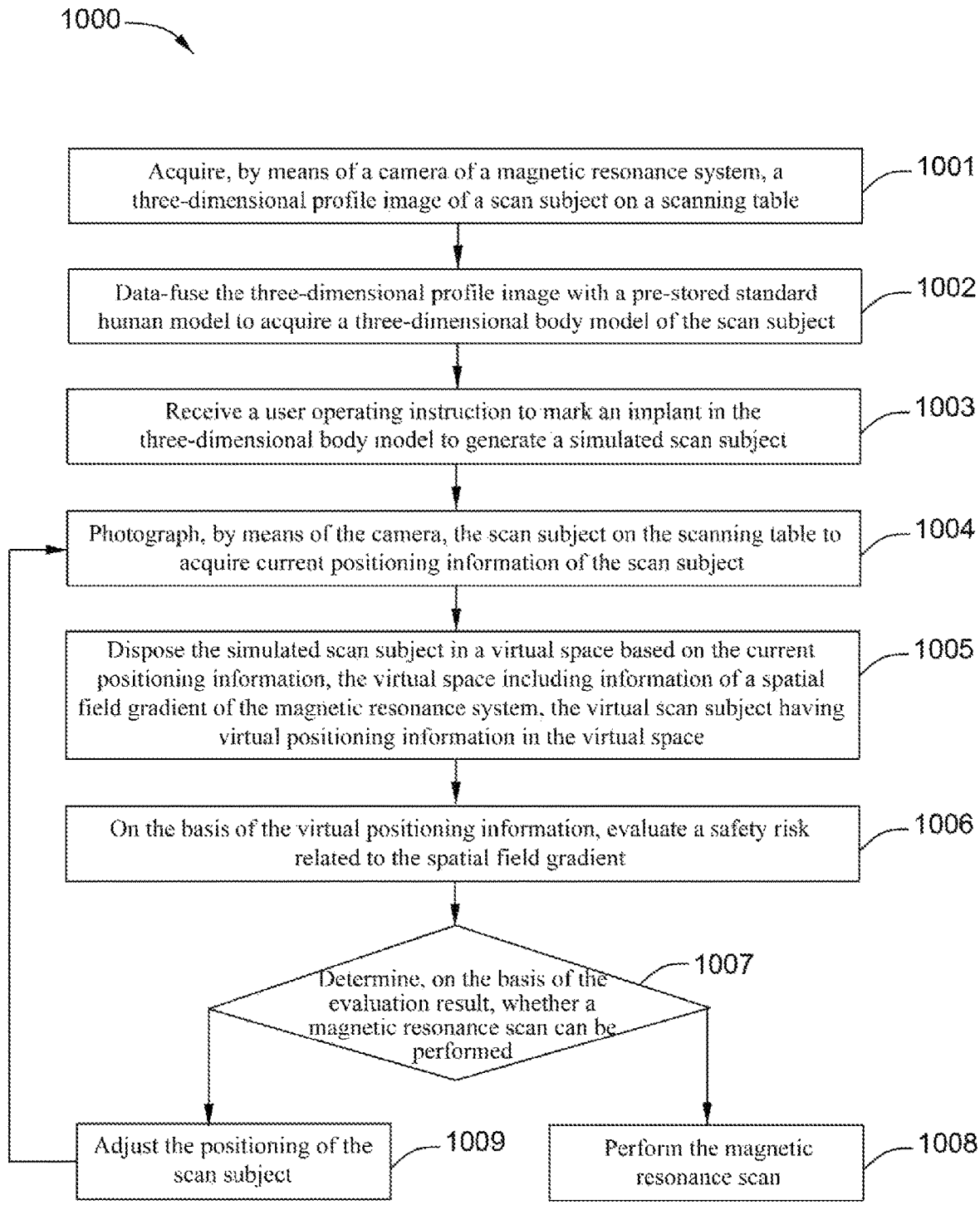
FIG. 10 illustrates an exemplary flowchart 1000 of a magnetic resonance scanning control method according to the present invention.

FIG. 10 illustrates a flowchart 1000 of an example of a magnetic resonance scanning control method of the present invention. In the method, in step 1101, a three-dimensional profile image of the scan subject on the scanning table 920 is acquired by means of the camera 950 of the magnetic resonance system. In step 1002, the three-dimensional profile image is data fused with a pre-stored standard human model to acquire a three-dimensional body model of the scan subject. In step 1003, the three-dimensional body model of the scan subject is displayed, and a user operating instruction is received to mark an implant in the three-dimensional body model to generate a simulated scan subject. In step 1004, the scan subject on the scanning table 920 is photographed by means of the camera 950 to acquire current positioning information of the scan subject, wherein the current positioning information may include location information and pose information of the scan subject on the scanning table 920. In step 1005, the simulated scan subject is disposed in a virtual space based on the current positioning information, the virtual space including information of a spatial field gradient of the magnetic resonance system, the virtual scan subject having virtual positioning information in the virtual space, and the virtual positioning information being consistent with the current positioning information. In step 1006, a safety risk related to the spatial field gradient is evaluated based on the virtual positioning information. In step 1007, it is determined whether a magnetic resonance scan can be performed based on the evaluation result. If yes, step 1008 is performed, that is, a magnetic resonance scan is performed. If not, step 1009 is performed, that is, the positioning of the scan subject is adjusted, and step 1004 is returned to. In step 1009, if the positioning of the scan subject cannot be further adjusted, the magnetic resonance scan may be terminated.

In an alternative solution of the above example, the three-dimensional profile image of the scan subject and the current positioning information of the scan subject may also be acquired in other manners, at which point a depth video camera may not need to be mounted, or other three-dimensional image acquisition devices may be mounted.

Based on the above description, an embodiment of the present invention may provide a magnetic resonance scanning control method, which may include: acquiring a three-dimensional body model of a scan subject; receiving a user operating instruction to mark an implant in the three-dimensional body model of the scan subject to generate a simulated scan subject; acquiring current positioning information of the scan subject on a scanning table, and determining, on the basis of the current positioning information, virtual positioning information of the simulated scan subject in a virtual space, the virtual space including distribution information of a spatial field gradient of the magnetic resonance system; and on the basis of the virtual positioning information, evaluating a safety risk related to the spatial field gradient.

In the method, the step of acquiring the three-dimensional body model of the scan subject may include: acquiring a three-dimensional profile image of the scan subject; and data-fusing the three-dimensional profile image with a pre-stored standard human model to acquire the three-dimensional body model of the scan subject.

The three-dimensional body model may include at least one body organ, and the standard human model may include at least one body organ.

In some embodiments, the scan subject positioned on the scanning table may be photographed by using a camera, to acquire the three-dimensional profile image of the scan subject.

In some embodiments, at least one among physiological information of the scan subject and a two-dimensional image of the scan subject is data-processed, to acquire the three-dimensional profile image of the scan subject.

In some embodiments, the at least one among the physiological information of the scan subject and the two-dimensional image of the scan subject may be inputted into a pre-trained deep learning network, to acquire the three-dimensional profile image of the scan subject.

The data-fusing may include: matching the three-dimensional profile image of the scan subject and the standard human model based on preset weight information of different body parts, to acquire the three-dimensional body model of the scan subject, the body parts including the at least one human organ.

The step of marking may further include: receiving basic information of the implant of the scan subject, and automatically marking the implant in the three-dimensional body model of the scan subject based on the basic information of the implant.

In the method, the basic information of the implant includes one or more among implantation location information, the size of the implant, and a safety parameter range of the implant.

The step of marking may further include: displaying, on a graphical user interface, the three-dimensional body model of the scan subject; and receiving an operational input of a user on the graphical user interface to add an implant identifier in the three-dimensional body model.

The step of marking may further include: adjusting at least one among the position, shape, and size of the marked implant based on the operation of the user on the graphical user interface.

The step of marking may further include: displaying, on the graphical user interface, the three-dimensional body model and the implant marked therein, and performing at least one among translating, scaling, and rotating operations on the marked implant in a three-dimensional coordinate system.

The step of marking may further include: performing at least one among translating, scaling, and rotating operations on the marked implant in at least one two-dimensional coordinates.

In some embodiments, the scanning table and the scan subject positioned on the scanning table may be photographed in real time to acquire the current positioning information.

In the method, the current positioning information includes a default positioning information of the scan subject on the scanning table.

The above-described step of "on the basis of the virtual positioning information, evaluating the safety risk" may include: estimating, based on the location information of the marked implant in the simulated scan subject and the virtual positioning information, a spatial field gradient that the implant passes during traveling of the scan subject.

The scanning control method may further include: displaying the simulated scan subject and contour lines of the spatial field gradient in the virtual space.

The scanning control method may further include: indicating the safety risk.

The scanning control method may further include: indicating, based on the safety risk, a positioning operation of the scan subject on the scanning table.

Some embodiments of the present invention further provide a magnetic resonance scanning control method for a magnetic resonance system. The magnetic resonance system includes a scanning table and a camera. The method includes: acquiring, by means of the camera, a three-dimensional profile image of a scan subject on the scanning table and data-fusing the three-dimensional profile image with a pre-stored standard human model to acquire a three-dimensional body model of the scan subject. The method also includes displaying the three-dimensional body model of the scan subject, and receiving a user operating instruction to mark an implant in the three-dimensional body model to generate a simulated scan subject. The method further includes photographing, by means of the camera, the scan subject on the scanning table to acquire current positioning information of the scan subject; disposing the simulated scan subject in a virtual space based on the current positioning information. The virtual space includes information of a spatial field gradient of the magnetic resonance system and the virtual scan subject includes virtual positioning information in the virtual space. The method also includes evaluating a safety risk related to the spatial field gradient on the basis of the virtual positioning information; and determining, based on the evaluation result, whether a magnetic resonance scan can be performed. If the magnetic resonance scan can be performed, then performing a magnetic resonance scan else adjusting the positioning of the scan subject, and returning to the step of acquiring the current positioning information of the scan subject.

Some embodiments of the present invention further provide a magnetic resonance system, including: a magnet assembly formed with a scanning cavity and a scanning table positioned relative to the magnet assembly and traveling in and out of the scanning cavity. The MR system also includes a scanning controller including operating instructions for performing the magnetic resonance scanning control method of any of the above embodiments.

The magnetic resonance system may further include a three-dimensional imaging device for acquiring the three-dimensional profile image of the scan subject positioned on the scanning table. The scanning controller is used for data-fusing the three-dimensional profile image with the pre-stored standard human model to acquire the three-dimensional body model of the scan subject, the standard human model including at least one human organ.

The three-dimensional imaging device may include a camera which is further configured to acquire the current positioning information of the scan subject on the scanning table.

The three-dimensional imaging device is disposed above the scanning table.

In embodiments of the present invention, by acquiring the three-dimensional body model of the scan subject, and marking the implant therein, the simulated scan subject close to the real scan subject is obtained. By determining the positioning information of the simulated scan subject in the virtual spatial field gradient, the safety risks related to the spatial field gradient are predicted, preventing an operator from positioning the scan subject by relying on experience. In addition, by predicting the safety risks by simulating a real scenario, the prediction is more accurate, the efficiency of magnetic resonance scan procedures can be increased, and safety problems due to implants being subjected to high spatial field gradients are effectively avoided.

Clause 1: A magnetic resonance scanning control method, including: acquiring a three-dimensional body model of a scan subject; a step of marking, wherein a user operating instruction is received to mark an implant in the three-dimensional body model of the scan subject to generate a simulated scan subject; acquiring current positioning information of the scan subject on a scanning table, and determining, on the basis of the current positioning information, virtual positioning information of the simulated scan subject in a virtual space, the virtual space including distribution information of a spatial field gradient of a magnetic resonance system; and on the basis of the virtual positioning information, evaluating a safety risk related to the spatial field gradient.

Clause 2: The method according to Clause 1, wherein the acquiring a three-dimensional body model of a scan subject includes: acquiring a three-dimensional profile image of the scan subject; and data-fusing the three-dimensional profile image with a pre-stored standard human model to acquire a three-dimensional body model of the scan subject.

Clause 3: The method according to Clause 2, wherein the three-dimensional body model includes at least one body organ, and the standard human model includes at least one body organ.

Clause 4: The method according to Clause 2, wherein the scan subject positioned on the scanning table is photographed using a camera, to acquire the three-dimensional profile image of the scan subject.

Clause 5: The method according to Clause 2, wherein at least one among physiological information of the scan subject and a two-dimensional image of the scan subject is data-processed, to acquire the three-dimensional profile image of the scan subject.

Clause 6: The method according to Clause 5, wherein the at least one among the physiological information of the scan subject and the two-dimensional image of the scan subject is inputted into a pre-trained deep learning network, to acquire the three-dimensional profile image of the scan subject.

Clause 7: The method according to Clause 2, wherein the data-fusing includes: matching the three-dimensional profile image of the scan subject and the standard human model based on preset weight information of different body parts, to acquire the three-dimensional body model of the scan subject, the body parts including the at least one human organ.

Clause 8: The method according to Clause 1, wherein the step of marking includes: receiving basic information of the implant of the scan subject, and automatically marking, on the basis of the basic information of the implant, the implant in the three-dimensional body model of the scan subject.

Clause 9: The method according to Clause 8, wherein the basic information of the implant includes one or more among implantation location information, the size of the implant, and a safety parameter range of the implant.

Clause 10: The method according to Clause 1, wherein the step of marking includes: displaying, on a graphical user interface, the three-dimensional body model of the scan subject; and receiving an operational input of a user on the graphical user interface to add an implant identifier in the three-dimensional body model.

Clause 11: The method according to Clause 10, wherein the step of marking includes: adjusting at least one among the position, shape, and size of the marked implant based on the operation of the user on the graphical user interface.

Clause 12: The method according to Clause 11, wherein the step of marking includes: displaying, on the graphical user interface, the three-dimensional body model and the implant marked therein, and performing at least one among translating, scaling, and rotating operations on the marked implant in a three-dimensional coordinate system.

Clause 13: The method according to Clause 11, wherein the step of marking includes: performing at least one among translating, scaling, and rotating operations on the implant marked in the three-dimensional body model in at least one two-dimensional coordinates.

Clause 14: The method according to Clause 1, wherein the scanning table and the scan subject positioned on the scanning table are photographed in real time to acquire the current positioning information.

Clause 15: The method according to Clause 1, wherein the current positioning information includes default positioning information of the scan subject on the scanning table.

Clause 16: The method according to Clause 1, wherein the step of evaluating the safety risk based on the virtual positioning information includes: estimating, based on the location information of the marked implant in the simulated scan subject and the virtual positioning information, a spatial field gradient that the implant passes during traveling of the scan subject.

Clause 17: The method according to Clause 1, wherein the method further includes: displaying the simulated scan subject and contour lines of the spatial field gradient in the virtual space.

Clause 18: The method according to Clause 1, wherein the method further includes: indicating the safety risk.

Clause 19: The method according to Clause 1, wherein the method further includes: indicating, based on the safety risk, a positioning operation of the scan subject on the scanning table.

Clause 20: A magnetic resonance scanning control method for a magnetic resonance system, the magnetic resonance system including a scanning table and a camera, and the method including: acquiring, by means of the camera, a three-dimensional profile image of a scan subject on the scanning table; data-fusing the three-dimensional profile image with a pre-stored standard human model to acquire a three-dimensional body model of the scan subject; displaying the three-dimensional body model of the scan subject, and receiving a user operating instruction to mark an implant in the three-dimensional body model to generate a simulated scan subject; photographing, by means of the camera, the scan subject on the scanning table to acquire current positioning information of the scan subject; disposing the simulated scan subject in a virtual space based on the current positioning information, the virtual space including information of a spatial field gradient of the magnetic resonance system, the virtual scan subject having virtual positioning information in the virtual space; on the basis of the virtual positioning information, evaluating a safety risk related to the spatial field gradient; and determining, based on the evaluation result, whether a magnetic resonance scan can be performed, if yes, then performing a magnetic resonance scan, and if not, then adjusting the positioning of the scan subject, and returning to the step of acquiring the current positioning information of the scan subject.

Clause 21: A magnetic resonance system, including: a magnet assembly formed with a scanning cavity; a scanning table positioned relative to the magnet assembly and traveling in and out of the scanning cavity; and a scanning controller including operating instructions for performing the magnetic resonance scanning control method of any of Clauses 1 to 20.

Clause 22: The system according to Clause 21, further including: a three-dimensional imaging device for acquiring the three-dimensional profile image of the scan subject positioned on the scanning table, wherein the scanning controller is used for data-fusing the three-dimensional profile image with the pre-stored standard human model to acquire the three-dimensional body model of the scan subject, the standard human model including at least one human organ.

Clause 23: The system according to Clause 22, wherein the three-dimensional imaging device includes a camera which is further configured to acquire the current positioning information of the scan subject on the scanning table.

Clause 24: The system according to Clause 22, wherein the three-dimensional imaging device is disposed above the scanning table.

While the present invention has been described in detail with reference to specific embodiments, it would be understood by those skilled in the art that many modifications and variations can be made to the present invention. Therefore, it should be understood that the claims are intended to cover all such modifications and variations within the true spirit and scope of the present invention.

The invention claimed is:

1. A magnetic resonance scanning control method, comprising:
   acquiring a three-dimensional body model of a scan subject;
   a step of marking, wherein a user operating instruction is received to mark an implant in the three-dimensional body model of the scan subject to generate a simulated scan subject;
   acquiring current positioning information of the scan subject on a scanning table, and determining, on the basis of the current positioning information, virtual positioning information of the simulated scan subject in a virtual space, the virtual space comprising distribution information of a spatial field gradient of a magnetic resonance system; and
   on the basis of the virtual positioning information, evaluating a safety risk related to the spatial field gradient.

2. The method according to claim 1, wherein the acquiring a three-dimensional body model of a scan subject comprises:
   acquiring a three-dimensional profile image of the scan subject; and
   data-fusing the three-dimensional profile image with a pre-stored standard human model to acquire a three-dimensional body model of the scan subject.

3. The method according to claim 2, wherein the three-dimensional body model comprises at least one body organ, and the standard human model comprises at least one body organ.

4. The method according to claim 2, wherein the scan subject positioned on the scanning table is photographed using a camera, to acquire the three-dimensional profile image of the scan subject.

5. The method according to claim 2, wherein at least one among physiological information of the scan subject and a two-dimensional image of the scan subject is data-processed, to acquire the three-dimensional profile image of the scan subject.

6. The method according to claim 5, wherein the at least one among the physiological information of the scan subject and the two-dimensional image of the scan subject is inputted into a pre-trained deep learning network, to acquire the three-dimensional profile image of the scan subject.

7. The method according to claim 2, wherein the data-fusing comprises:
   matching the three-dimensional profile image of the scan subject and the standard human model based on preset weight information of different body parts, to acquire the three-dimensional body model of the scan subject, the body parts comprising the at least one human organ.

8. The method according to claim 1, wherein the step of marking comprises:
   receiving basic information of the implant of the scan subject, and automatically marking, on the basis of the basic information of the implant, the implant in the three-dimensional body model of the scan subject.

9. The method according to claim 8, wherein the basic information of the implant comprises one or more among implantation location information, the size of the implant, and a safety parameter range of the implant.

10. The method according to claim 1, wherein the step of marking comprises:
    displaying, on a graphical user interface, the three-dimensional body model of the scan subject; and
    receiving an operational input of a user on the graphical user interface to add an implant identifier in the three-dimensional body model.

* * * * *